United States Patent [19]

Fuchs et al.

[11] Patent Number: 5,208,365
[45] Date of Patent: May 4, 1993

[54] PROCESS FOR THE PREPARATION OF 2,5-DI(PHENYLAMINO)-TEREPHTHALIC ACID AND ITS DIALKYL ESTERS IN HIGH PURITY

[75] Inventors: Hermann Fuchs, Königstein/Taunus; Walter Gilb; Otto Arndt, both of Hofheim am Taunus, all of Fed. Rep. of Germany

[73] Assignee: Hoechst Aktiengesellschaft, Frankfurt am Main, Fed. Rep. of Germany

[21] Appl. No.: 898,201

[22] Filed: Jun. 11, 1992

[30] Foreign Application Priority Data

Jun. 14, 1991 [DE] Fed. Rep. of Germany ....... 4119601

[51] Int. Cl.$^5$ ............................................. C07C 229/00
[52] U.S. Cl. ........................................ 560/48; 562/457
[58] Field of Search ......................... 560/48; 562/457

[56] References Cited

U.S. PATENT DOCUMENTS

| | | |
|---|---|---|
| 3,124,581 | 3/1964 | Bohler et al. ............................ 560/48 |
| 3,413,313 | 11/1968 | Scherrer ................................. 560/48 |
| 3,413,339 | 11/1968 | Scherrer ................................. 560/48 |

FOREIGN PATENT DOCUMENTS

| | | |
|---|---|---|
| 1539553 | 9/1968 | France . |
| 935525 | 8/1963 | United Kingdom . |

Primary Examiner—Paul J. Killos

[57] ABSTRACT

A process for the preparation of 2,5-di(phenylamino)-terephthalic acid and its dialkyl esters of formula (I):

in which R is a hydrogen atom or a methyl group and R' is a hydrogen atom or a methyl or ethyl group.

7 Claims, No Drawings

PROCESS FOR THE PREPARATION OF 2,5-DI(PHENYLAMINO)-TEREPHTHALIC ACID AND ITS DIALKYL ESTERS IN HIGH PURITY

The present invention relates to a technologically advantageous process for the preparation of 2,5-di(phenylamino)terephthalic acid and its dialkyl esters of formula (I):

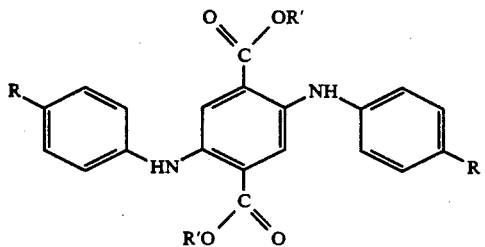

in which R is a hydrogen atom or a methyl group and R' is a hydrogen atom or a methyl or ethyl group.

It is known to prepare 2,5-di(phenylamino)terephthalic acid and its dialkyl esters in accordance with a multistage process by cyclizing a dialkyl succinate to the dialkyl 2,5-dihydroxycyclohexadiene-1,4-dicarboxylate in the manner of a Dieckmann or double Claisen condensation (Fortschr. chem. Forschung, vol. 1 (1950) 685–724), then converting the product to the dialkyl 2,5-di(phenylamino)-3,6-dihydroterephthalate by means of a condensation reaction with a primary phenylamine (for example aniline or toluidine) in xylene or ethylbenzene or in mixtures thereof, in the presence of an aliphatic acid (for example acetic acid), dehydrogenating (oxidizing) the product to the dialkyl 2,5-di(phenylamino)terephthalate, then saponifying this ester under alkaline conditions (e.g. in alcoholic sodium hydroxide solution) and liberating the 2,5-di(phenylamino)terephthalic acid by treating the resulting disodium 2,5-di(phenylamino)terephthalate with acid.

The literature describing the preparation of di(phenylamino)terephthalic acid from a succinic acid ester by the method stated above (Japanese patent 49-108 036; U.S. Pat. Nos. 3,555,087, 3,671,451 and 4,981,997) includes a number of process parameters such as, for example, the solvents, the intermediate isolation of individual or all products of the synthetic stages (such as (1) dialkyl succinylosuccinate, (2) dialkyl 2,5-di(phenylamino)-3,6-dihydroterephthalate, (3) dialkyl 2,5-di(phenylamino)terephthalate and (4) 2,5-di(phenylamino)terephthalic acid), the type of catalysts used, if appropriate with additives for the above-mentioned intermediate stages (1), (2) and (3), the sequence of oxidation and saponification (saponification simultaneous with or subsequent to oxidation), the dehydrogenating (oxidizing) agents (such as, for example, nitrobenzene and derivatives thereof, quinones, oxygen, iodine) and the working-up of the auxiliaries used (such as, for example, solvents, phenylamine (aniline, p-toluidine), catalysts, additives).

The present invention thus relates to a process for the preparation of 2,5-di(phenylamino)terephthalic acid and its dialkyl esters of formula (I), in which R is a hydrogen atom or a methyl or ethyl group, by (1) reacting a dialkyl ($C_1$–$C_2$) succinate with a sodium alcoholate in xylene, in the manner of a Dieckmann condensation, to give the disodium salt of the dialkyl($C_1$–$C_2$) 2,5-dihydroxycyclohexadiene-1,4-dicarboxylate, (2) reacting the resulting condensation product, after decomposition of the disodium salt with acid, with a phenylamine of formula (II),

in which R is as defined above, in the presence of an organic acid, in xylene, to give the dialkyl($C_1$–$C_2$) 2,5-di(phenylamino)-3,6-dihydroterephthalate, (3) dehydrogenating (oxidizing) the resulting 1,4-cyclohexadiene derivative with oxygen to give the corresponding dialkyl($C_1$–$C_2$) 2,5-di(phenylamino)terephthalate, (4) saponifying the resulting dialkyl ester in methanolic sodium hydroxide solution to give the corresponding disodium 2,5-di(phenylamino)terephthalate, and (5) liberating the 2,5-di(phenylamino)terephthalic acid from said disodium salt with acid, which process comprises carrying out the oxidation in stage (3) in such a way that the reaction mixture of stage (2), in the form of a solution or suspension, is blanketed with nitrogen in a stirred vessel, this reaction mixture is circulated by pumping and the oxygen is metered into a partial volume of the circulated reaction mixture in such a way as to produce effective thorough mixing.

The oxygen can be metered in on its own or mixed with inert gases, e.g. in the form of air. The xylene can be used on its own or in the form of technical-grade xylene mixtures.

Propionic acid or hexafluoropropanesulfonic acid, for example, can be used as the acid catalyst for the reaction with the phenylamine of formula II in stage (2).

It is furthermore advantageous if solid particles still present in the suspension are comminuted at the same time as the oxygen is metered in.

Both the effective thorough mixing of the circulated reaction mixture, present in the partial volume, with the oxygen, and the comminution of any crystals present, can advantageously be brought about by cavitation effects produced for example by a rotary homogenizer.

When a rotary homogenizer with nozzle feed is used, the operating space of this pump, into which the gas is metered through an inlet, is at one and the same time the partial volume in which the reaction takes place. The operating space is made up of a meshing rotor-stator system. The rotors and stators possess passages, for example in the form of slots or cylindrical channels. The passages fill with material to be processed, in the form of a solution or suspension of 2,5-di(phenylamino)-3,6-dihydroterephthalic acid ester, and gaseous oxygen fed in through a nozzle. The rotor, rotating at high speed, presses the material to be processed through the passages into the stator chambers by means of the high centrifugal acceleration. During the filling process, the stator chambers are closed by the next largest rotor ring so that the material to be processed cannot escape. A substantial overpressure prevails in the stator chambers and is shock-relieved within fractions of a second by the continuing rotation of the rotor. This brings about extreme cavitation effects, affording an exceptionally effective distribution of the oxygen. At the same time, suspended crystals of 2,5-di(phenylamino)-3,6-dihydroterephthalic acid ester are efficiently comminuted, thereby considerably enlarging their specific surface area and hence increasing the reaction rate.

In the process according to the invention, the use of a catalyst can be dispensed with during the oxidation, which constitutes a particular advantage. It is also possible, however, to use a catalyst of V4A steel and/or of a transition metal of the periodic table of the elements, such as, for example, molybdenum or vanadium, and/or of a rare earth metal with variable oxidation levels, such as, for example, samarium or compounds thereof, such as, for example, samarium(III) oxide, or mixtures thereof.

One advantage of the process according to the invention is the relatively short reaction time combined with favorable space-time yields. This is based inter alia on the fact that the partial volume in which the reaction with the oxygen takes place is very much smaller than the volume of the stirred vessel, which unavoidably has to be sufficiently large to be able to accommodate the whole of the product of stage (2) obtained in the combined production process. Indeed, on account of its smaller size, such a partial volume can have an explosion-proof design without greater expense and hence can permit a very much greater oxygen content than that of less than 8% by volume which is permissible for the gas mixture over the reaction mixture in the stirred vessel and in the circulating gas. This increases the concentration of dissolved oxygen in the solution or suspension and with it the reaction rate.

The procedure according to the invention affords an optimum comminution of the gas bubbles and hence a larger area over which the exchange between gas and liquid can take place, thereby further shortening the reaction time by about 60 to 65%.

The increased reaction rate is advantageous particularly because it enables optimum cycle times to be attained for the appropriate further processing in the transition from stage (2) to (3) and subsequently to stage (4).

As the reaction time is also dependent on the size of the partial volume, it can be controlled in this way so that optimum cycle times can be maintained.

EXAMPLES 1. 230 kg of xylene and 27 kg of propionic acid were placed in a 600 l stirred vessel and the mixture was stirred. After the addition of 34.2 kg (150 mol) of methyl succinate, the mixture was heated to 60° C. and 38.7 kg (361 mol) of p-toluidine, molten at 80° C., were then introduced by suction. The gas space over this reaction mixture was flushed 3 times with nitrogen and the batch was boiled, while circulating, until the condensation water had been completely removed from the circuit. The temperature in the vessel was adjusted to 100° C. and the reaction mixture was circulated by pumping. A rotary homogenization pump is switched into the circuit of the circulated reaction mixture. Approx. 11 m³/h were circulated, i.e. the contents of the stirred vessel (approx. 370 l) were circulated approx. 30 times per hour. The oxygen was metered into the rotary homogenization pump in such a way that the oxygen content in the circulating gas remained below 8% by volume. At the same time, the water formed during the oxidation was distilled off azeotropically. The oxidation was complete after 4.5 to 5 hours. 3.3 to 3.6 kg of oxygen (theory 2.4 kg) were consumed and 3.7 to 4.1 kg of water (theory 2.7 kg) were removed from the system.

The yield of dimethyl 2,5-di(p-toluidino)terephthalate was 98 to 99% of theory (determination by HPLC analysis in the reaction solution as area percentages).

2. Example 1 was repeated except that the p-toluidine was replaced with 33.6 kg (361 mol) of aniline. The oxidation was complete after approx. 5 hours. Approx. 3.3 kg of oxygen were consumed and approx. 3.5 kg of water were removed from the system.

The yield of dimethyl 2,5-di(phenylamino)terephthalate was over 98% of theory (determination by HPLC analysis as in Example 1).

3. A technical-grade crude solution of methyl succinate in xylene, as obtained in the production process, was placed in a 600 l stirred vessel. It contained 34.2 kg (150 mol) of methyl succinate, and xylene was added in an amount such as to give a concentration of 12.9% of methyl succinate, analogous to Example 1. After the addition of 22.4 kg of propionic acid, the mixture was heated to 60° C. and 33.9 kg (316 mol) of p-toluidine, molten at 80° C., were then introduced by suction. The subsequent procedure was as in Example 1. The oxidation was complete after 6 hours. 3.6 kg of oxygen were consumed and 4.2 kg of water were removed from the system.

The yield of dimethyl 2,5-di(p-toluidino)terephthalate was over 98% of theory (determination by HPLC analysis as in Example 1).

4. A technical-grade crude solution of methyl succinate in xylene, as obtained in the production process, was placed in a 1500 l stirred vessel. It contained 113.3 kg (496.5 mol) of methyl succinate, and xylene was added in an amount such as to give a concentration of 12.9% of methyl succinate, analogous to Example 1. After the addition of 77.2 kg of propionic acid, the mixture was heated to 60° C. and 112 kg (1044.8 mol) of p-toluidine, molten at 80° C., were then introduced by suction. The gas space over the reaction mixture was flushed 3 times with nitrogen and the batch was boiled, while circulating, until the condensation water had been completely removed from the circuit. The temperature of the reaction mixture in the vessel was adjusted to 100° C. and the rotary homogenization pump was switched on. Approx. 8.5 m³/h were circulated, i.e. the contents of the stirred vessel were circulated approx. 7 times per hour. The subsequent procedure was as in Example 1. Although the volume circulated per hour by the rotary homogenizer was only approx. 30%, because of the batch being 3.3 times larger than in Example 3, the oxidation was already complete after 13 hours. 11.8 kg of oxygen (theory 7.95 kg) were consumed.

The yield of dimethyl 2,5-di(p-toluidino)terephthalate was over 98% (determination by HPLC analysis as in Example 1).

What is claimed is:

1. A process for the preparation of 2,5-di(phenylamino) terephthalic acid, or its dialkyl esters, of formula (I):

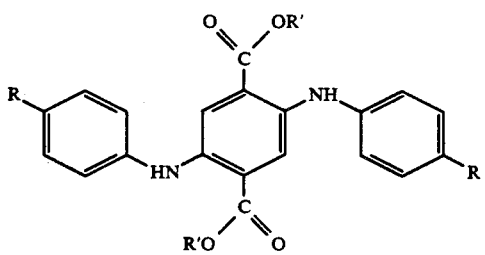

in which R is a hydrogen atom or a methyl group and R' is a hydrogen atom or a methyl or ethyl group, said process comprising (1) reacting a dialkyl($C_1$–$C_2$) succinate with a sodium alcoholate in xylene, in the manner of a Dieckmann condensation, to give the disodium salt of the dialkyl ($C_1$–$C_2$)2,5-dihydroxycyclohexadiene-1,4-dicarboxylate, (2) reacting the resulting condensation product, after decomposition of the disodium salt with acid, with a phenylamine of formula (II):

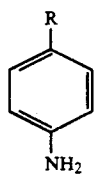

in which R is as defined above, in the presence of an organic acid, in xylene, to give the dialkyl($C_1$–$C_2$) 2,5-di(phenylamino)-3,6-dihydroterephthalate, (3) dehydrogenating (oxidizing) the resulting 1,4-cyclohexadiene derivative with oxygen to give the corresponding dialkyl($C_1$–$C_2$) 2,5-di(phenylamino)-terephthalate, said steps (1) through (3) being optionally carried out without isolation of any of the intermediate products, and then (4) optionally saponifying the resulting dialkyl ester in methanolic sodium hydroxide solution to give the corresponding disodium 2,5-di(phenylamino) terephthalate, and (5) optionally liberating the 2,5-di(phenylamino) terephthalic acid from said disodium salt with acid, and wherein said process further comprises carrying out the oxidation in stage (3) in such a way that the reaction mixture of stage (2), in the form of a solution or suspension containing solid particles, is blanketed with nitrogen in a stirred vessel, this reaction mixture is circulated by pumping and the oxygen is metered into a partial volume of the circulated reaction mixture in such a way as to produce effective thorough mixing.

2. The process as claimed in claim 1, wherein solid particles present are comminuted at the same time as the oxygen is metered in.

3. The process as claimed in claim 1, wherein the thorough mixing of the reaction mixture with the oxygen and/or the comminution of the solid particles or the mixing and comminution are brought about by cavitation effects.

4. The process as claimed in claim 1, wherein the partial volume into which the oxygen is metered is the operating space of a rotary homogenization pump.

5. A process for the preparation of a 2,5-di(phenylamino) terephthalic acid ester of formula (I):

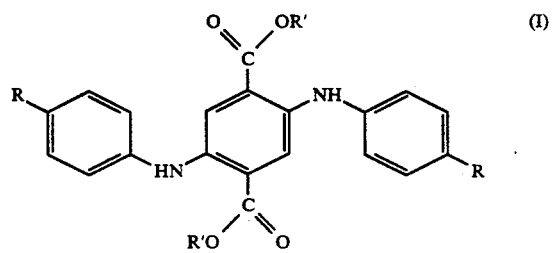

in which R is a hydrogen atom or a methyl group and R' is a methyl or ethyl group, the process comprising circulating a reaction mixture comprising a solution or suspension of 2,5-di(phenylamino)-3,6-dihydroterephthalic acid ester within a vessel under an atmosphere of nitrogen and supplying a gas comprising oxygen to a partial volume of the circulated reaction mixture in such a way as to produce effective thorough mixing of the oxygen with the reaction mixture, thereby dehydrogenating, through oxidation, said 2,5-di(phenylamino)-3,6-dihydroterephthalic acid ester to obtain the corresponding compound of said formula (I).

6. The process as claimed in claim 5, wherein said corresponding compound of said formula (I) is saponified with sodium hydroxide to give the corresponding disodium salt.

7. The process as claimed in claim 6, wherein said corresponding disodium salt is treated with an acid to liberate 2,5-di(phenylamino) terephthalic acid.

* * * * *